(12) United States Patent
Araki et al.

(10) Patent No.: US 7,829,703 B2
(45) Date of Patent: Nov. 9, 2010

(54) DIFLUOROMETHANESULFONYL ANILIDE DERIVATIVES USEFUL AS HERBICIDES

(75) Inventors: Koichi Araki, Ushiku (JP); Sachio Kudo, Tsukuba (JP); Yoshitaka Sato, Tsukuba (JP); Keiji Endo, Inashiki-gun (JP); Shinichi Shirakura, Oyama (JP); Shin Nakamura, Oyama (JP)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/190,703

(22) Filed: Aug. 13, 2008

(65) Prior Publication Data

US 2008/0312084 A1 Dec. 18, 2008

Related U.S. Application Data

(62) Division of application No. 10/594,570, filed as application No. PCT/EP2005/002952 on Mar. 19, 2005, now Pat. No. 7,482,308.

(30) Foreign Application Priority Data

| Apr. 1, 2004 | (JP) | ............................. 2004-109197 |
| Jul. 22, 2004 | (JP) | ............................. 2004-214777 |
| Dec. 8, 2004 | (JP) | ............................. 2004-355616 |

(51) Int. Cl.
C07D 251/20 (2006.01)
A01N 43/66 (2006.01)
C07D 239/52 (2006.01)
A01N 43/54 (2006.01)

(52) U.S. Cl. ..................................... 544/219; 504/227
(58) Field of Classification Search ................. 544/219; 504/227
See application file for complete search history.

(56) References Cited

U.S. PATENT DOCUMENTS

| 5,559,081 A | 9/1996 | Gates et al. |
| 5,885,935 A * | 3/1999 | Gates et al. ................. 504/230 |
| 6,458,748 B1 * | 10/2002 | Yoshimura et al. .......... 504/243 |
| 2007/0219199 A1 | 9/2007 | Araki et al. |
| 2009/0305894 A1 | 12/2009 | Araki et al. |

FOREIGN PATENT DOCUMENTS

| EP | 1 101 760 A1 | 5/2001 |
| JP | 11-60562 | 3/1999 |
| JP | 2000-44546 A | 2/2000 |
| WO | WO 93/09099 A2 | 5/1993 |
| WO | WO 96/41799 A1 | 12/1996 |

OTHER PUBLICATIONS

International Preliminary Report on Patentability for Application No. PCT/EP2005/002952, European Patent Office, Netherlands, mailed on May 15, 2006.
International Search Report for International Application No. PCT/EP2005/002952, European Patent Office, Netherlands, mailed on Nov. 7, 2005.
English language abstract of JP 11-60562, Mar. 2, 1999.
English language abstract of JP 2004-44546 A, published on Feb. 15, 2000 (listed as document FP5 on accompanying form PTO/SB/08A).
Office Action mailed Aug. 10, 2009, in U.S. Appl. No. 11/632,832, Araki, K., et al., filed Mar. 19, 2007.
Office Action mailed Oct. 16, 2008, in U.S. Appl. No. 11/632,832, Araki, K., et al., filed Mar. 19, 2007.
Office Action mailed Apr. 29, 2008, in U.S. Appl. No. 11/632,832, Araki, K., et al., filed Mar. 19, 2007.
Co-pending Application, U.S. Appl. No. 12/066,940, inventors Araki, K., et al., filed on Aug. 5, 2009 (Not Published).
Office Action mailed Apr. 7, 2010, in U.S. Appl. No. 11/632,832, Araki, K. et al., filed March 19, 2007.

* cited by examiner

Primary Examiner—Venkataraman Balasubramanian
(74) Attorney, Agent, or Firm—Sterne, Kessler, Goldstein & Fox P.L.L.C.

(57) ABSTRACT

Novel difluoromethanesulfonamide derivatives of the formula (I) Difluoromethanesulfonamide derivatives represented by the formula

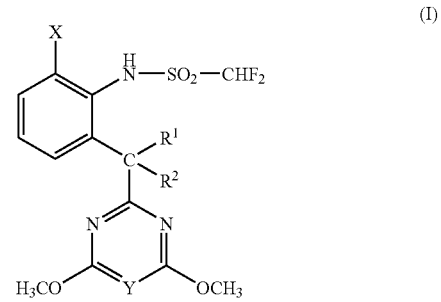

wherein
X represents halogen,
Y represents CH or N,
$R^1$ represents hydrogen, and
$R^2$ represents hydrogen or hydroxy, or
$R^1$ and $R^2$ together may form C=O with the carbon atom to which they are bonded,
and their use as herbicide for paddy field weeds.

7 Claims, No Drawings

DIFLUOROMETHANESULFONYL ANILIDE DERIVATIVES USEFUL AS HERBICIDES

This application is a divisional of application Ser. No. 10/594,570, filed Sep. 27, 2006, now U.S. Pat. No. 7,482,308, which is a National Stage of International Application No. PCT/EP2005/002952, filed Mar. 19, 2005, which claims the benefit of Japanese Patent Application No. 2004-109197, filed Apr. 1, 2004, Japanese Patent Application No. 2004-214777, filed Jul. 22, 2004 and Japanese Patent Application No. 2004-355616, filed Dec. 8, 2004. The entirety of each of these applications is incorporated by reference herein.

The present invention relates to novel difluoromethanesulfonamide derivatives, to process for their preparation and to their use as herbicides.

It has been already known that certain sulfonamide derivatives show an action as herbicide (for example, WO 93/09099, WO 96/41799, Japanese Laid-open Patent Application No. 60562/1999 and Japanese Laid-open Patent Application No. 44546/2000).

In developing a herbicide, a problem of controlling weeds which express resistance against existing herbicides, for example, SU resistant weeds (sulfonylurea resistant weeds) has been recently taken up as one of the important subjects. The development of an herbicide, that can control these resistant weeds and other annual and perennial weeds at the same time with a single ingredient, has been requested.

According to the invention there have been found the following compounds of formula (I)

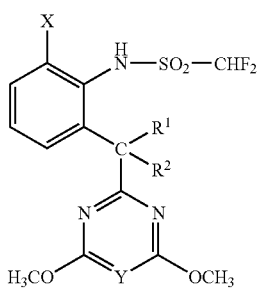

(I)

wherein
X represents halogen,
Y represents CH or N,
R¹ represents hydrogen, and
R² represents hydrogen or hydroxy, or
R¹ and R² together with the carbon atom to which they are bonded may form C=O.

The compounds of the formula (I), according to the invention, can be obtained by a process in which
a) compounds of the formula (II)

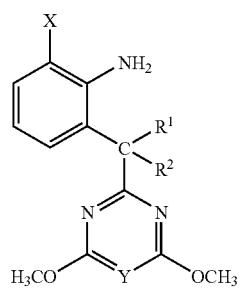

(II)

wherein
X, Y, R¹ and R² have the same definition as aforementioned, are reacted with difluoromethanesulfonyl chloride in the presence of inert solvents, and if appropriate, in the presence of an acid binding agent, or
b) in case that R¹ and R² together with the carbon atom to which they are bonded form C=O:
compounds of the formula (Ib)

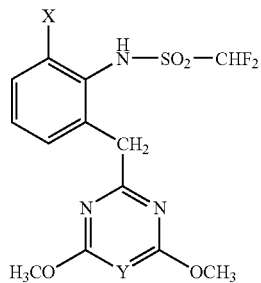

(Ib)

wherein
X and Y have the same definition as aforementioned, are reacted with an oxidizing agent in the presence of inert solvents, and if appropriate, in the presence of an acid catalyst, or
c) in case that R¹ represents hydrogen, and R² represents hydroxy:
compounds of the formula (Ic)

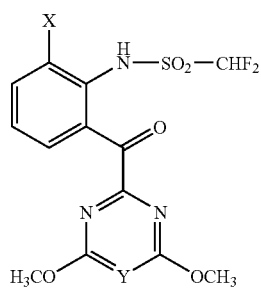

(Ic)

wherein
X and Y have the same definition as aforementioned, are reacted with an alkali metal hydride complex compound or a borane complex in the presence of inert solvents.

The difluoromethanesulfonamide derivatives of the formula (I), according to the present invention show strong herbicidal activities.

Though the difluoromethanesulfonamide derivatives of the formula (I) are included conceptually in the compounds of the general formula described in WO 96/41799, the compounds of the formula (I) are novel compounds, which are not specifically disclosed in said reference. And the compounds of the formula (I) unexpectedly show an extremely strong herbicidal action, compared with known compounds with similar structure described specifically in WO 96/41799. They show remarkably excellent herbicidal action particularly against paddy field weeds and at the same time show excellent herbicidal effect against sulfonylurea resistant weeds, which is a biological effect that is not described in WO 96/41799.

The difluoromethanesulfonamide derivatives of the formula (I), according to present invention are, therefore, useful particularly as herbicides for paddy field.

In the present specification, "halogen" represents fluorine, chlorine, bromine or iodine, preferably represents fluorine or chlorine.

In the compounds of the aforementioned formula (I), preferably,

X represents fluorine or chlorine,

Y represents CH or N, $R^1$ represents hydrogen, and $R^2$ represents hydrogen or hydroxy, or $R^1$ and $R^2$ together may form C=O with the carbon atom to which they are bonded.

The aforementioned preparation process (a) can be illustrated by the following reaction scheme in case that, for example, 2-fluoro-6-[(4,6-dimethoxypyrimidin-2-yl)-hydroxymethyl] aniline and difluoromethanesulfonyl chloride are used as the starting materials.

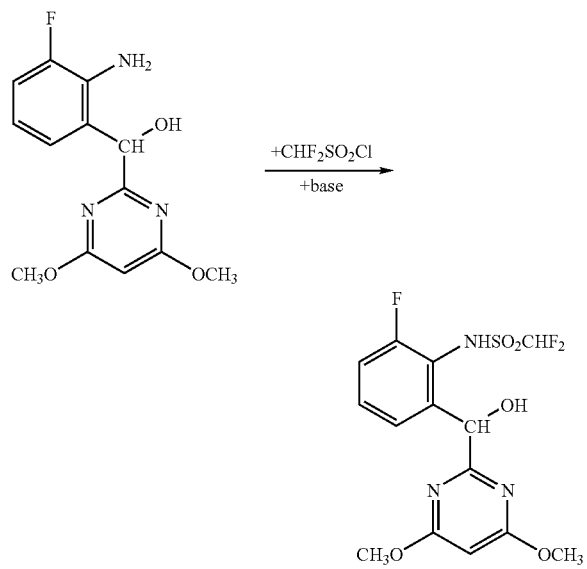

The aforementioned preparation process (b) can be illustrated by the following reaction scheme in case that, for example 2-fluoro-6-[(4,6-dimethoxypyrimidin-2-yl)-methyl]-N-difluoromethanesulfonanilide is used as the starting material and chromium (VI) oxide is used as oxidizing agent.

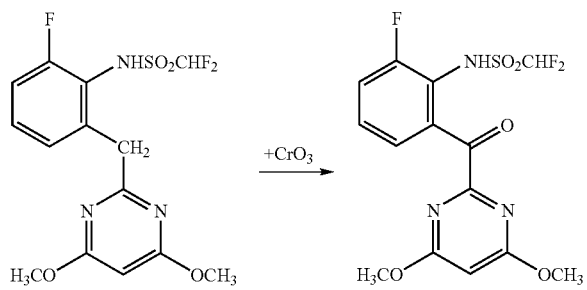

The aforementioned preparation process (c) can be illustrated by the following reaction scheme in case that, for example 2-fluoro-6-[(4,6-dimethoxypyrimidin-2-yl)-carbonyl]-N-difluoromethanesulfonanilide is used as the starting material and sodium borohydride is used as alkali metal hydride complex compound.

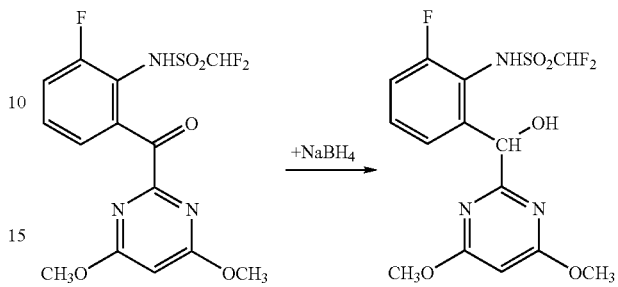

The compounds, in case that $R^1$ and $R^2$ together form C=O with the carbon atom to which they are bonded, in the compounds of the formula (II) used as the starting materials in the aforementioned preparation process (a), include the known compounds described in WO 96/41799 and can be easily prepared, for example, according to the process described in said reference.

Further, the compounds, in case that $R^1$ represents hydrogen and $R^2$ represents hydroxy in the compounds of the aforementioned formula (II), include known compounds described in Japanese Laid-open Patent Application No. 60562/1999 and can be easily prepared, for example, by reacting the compounds, in case that $R^1$ and $R^2$ together with the carbon atom to which they are bonded form C=O, in the aforementioned formula (II), with a metal hydride complex compound, for example, sodium borohydride, lithium aluminium hydride, etc., according to the process described in the same reference.

The compounds, in case that $R^1$ and $R^2$ both represent hydrogen in the compounds of the aforementioned formula (II), include known compounds described in WO 96/41799 and can be easily prepared, for example, by reacting a compound of the formula

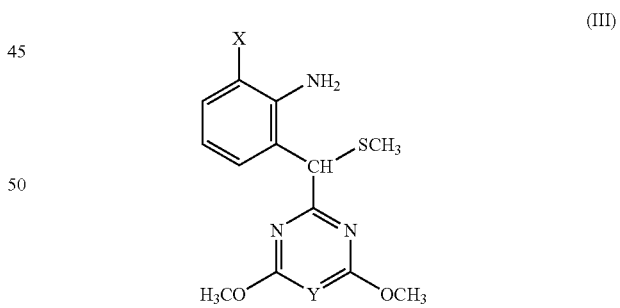

(III)

wherein

X and Y have the same definition as aforementioned, with a reducing agent, for example, sodium borohydride in the presence of nickel (II) chloride, or by reacting with Raney nickel, according to the process described in the same literature.

The compounds of the above-mentioned formula (III) include the known compounds described in the aforementioned patent references and can be easily prepared, for example, according to the process described in the same literature.

As specific examples of the compounds of the formula (II), used as the starting materials in the aforementioned preparation process (a), the following can be mentioned:
2-fluoro-6-[(4,6-dimethoxypyrimidin-2-yl)methyl]aniline,
2-chloro-6-[(4,6-dimethoxypyrimidin-2-yl)methyl]aniline,
2-bromo-6-[(4,6-dimethoxypyrimidin-2-yl)methyl]aniline,
2-iodo-6-[(4,6-dimethoxypyrimidin-2-yl)methyl]aniline,
2-fluoro-6-[(4,6-dimethoxypyrimidin-2-yl)hydroxymethyl] aniline,
2-chloro-6-[(4,6-dimethoxypyrimidin-2-yl)hydroxymethyl] aniline,
2-bromo-6-[(4,6-dimethoxypyrimidin-2-yl)hydroxymethyl] aniline,
2-iodo-6-[(4,6-dimethoxypyrimidin-2-yl)hydroxymethyl] aniline,
2-fluoro-6-[(4,6-dimethoxypyrimidin-2-yl)carbonyl]aniline,
2-chloro-6-[(4,6-dimethoxypyrimidin-2-yl)carbonyl] aniline,
2-bromo-6-[(4,6-dimethoxypyrimidin-2-yl)carbonyl] aniline,
2-iodo-6-[(4,6-dimethoxypyrimidin-2-yl)carbonyl]aniline,
2-fluoro-6-[(4,6-dimethoxytriazin-2-yl)methyl]aniline,
2-chloro-6-[(4,6-dimethoxytriazin-2-yl)methyl]aniline,
2-bromo-6-[(4,6-dimethoxytriazin-2-yl)methyl]aniline,
2-iodo-6-[(4,6-dimethoxyrtiazin-2-yl)methyl]aniline,
2-fluoro-6-[(4,6-dimethoxytriazin-2-yl)hydroxymethyl] aniline,
2-chloro-6-[(4,6-dimethoxytriazin-2-yl)hydroxymethyl] aniline,
2-bromo-6-[(4,6-dimethoxytriazin-2-yl)hydroxymethyl] aniline,
2-iodo-6-[(4,6-dimethoxyrtiazin-2-yl)hydroxymethyl] aniline,
2-fluoro-6-[(4,6-dimethoxytriazin-2-yl)carbonyl]aniline,
2-chloro-6-[(4,6-dimethoxytriazin-2-yl)carbonyl]aniline,
2-bromo-6-[(4,6-dimethoxytriazin-2-yl)carbonyl]aniline,
2-iodo-6-[(4,6-dimethoxyrtiazin-2-yl)carbonyl]aniline, and so on.

The compounds of the formula (Ib), used as the starting materials in the aforementioned preparation process (b), correspond to a part of the compounds of the formula (I) of the present invention which can be prepared by the aforementioned preparation process (a) and as their specific examples the following can be mentioned:
2-fluoro-6-[(4,6-dimethoxypyrimidin-2-yl)methyl]-N-difluoromethanesulfonanilide,
2-chloro-6-[(4,6-dimethoxypyrimidin-2-yl)methyl]-N-difluoromethanesulfonanilide,
2-bromo-6-[(4,6-dimethoxypyrimidin-2-yl)methyl]-N-difluoromethanesulfonanilide,
2-fluoro-6-[(4,6-dimethoxytriazin-2-yl)methyl]-N-difluoromethanesulfonanilide, and so on.

As oxidizing agent used for the oxidation of the compounds of the above-mentioned formula (Ib) in the aforementioned preparation process (b) there can be mentioned, for example, chromium (VI) oxide, manganese dioxide, selenium dioxide, selenium dioxide and so on.

The compounds of the formula (Ic), used as starting materials in the aforementioned preparation process (c), correspond to a part of the compounds of the formula (I) of the present invention which can be prepared by the aforementioned preparation processes (a) or (b) and as their specific examples the following can be mentioned:
2-fluoro-6-[(4,6-dimethoxypyrimidin-2-yl)carbonyl]-N-difluoromethanesulfonanilide,
2-chloro-6-[(4,6-dimethoxypyrimidin-2-yl)carbonyl]-N-difluoromethanesulfonanilide,
2-bromo-6-[(4,6-dimethoxypyrimidin-2-yl)carbonyl]-N-difluoromethanesulfonanilide,
2-iodo-6-[(4,6-dimethoxypyrimidin-2-yl)carbonyl]-N-difluoromethanesulfonanilide,
2-fluoro-6-[(4,6-dimethoxytriazin-2-yl)carbonyl]-N-difluoromethanesulfonanilide, etc.

As alkali metal hydride complex compounds used for the hydrogenation of the compounds of the formula (Ic) in the aforementioned preparation process (c) there can be mentioned, for example, sodium borohydride, lithium aluminium hydride, etc., and as borane complex there can be mentioned, for example, dimethyl sulfide borane, pyridine-borane, and so on.

The reaction of the above-mentioned preparation process (a) can be conducted in an appropriate diluent. As examples of the diluent used in that case there can be mentioned aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl isopropyl ketone, methyl isobutyl ketone (MIBK), etc.; nitrites, for example, acetonitrile, propionitrile, etc.; esters, for example, ethyl acetate, amyl acetate, etc.; bases, for example, pyridine etc.

The preparation process (a) can be conducted in the presence of an acid binding agent. As said acid binder there can be mentioned, as inorganic base, hydrides, hydroxides, carbonates, bicarbonates, etc. of alkali metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide, etc.; inorganic alkali metal amides, for example, lithium amide, sodium amide, potassium amide, etc.; as organic base, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo [2,2,2]octane (DABCO), 1,8-diazabicyclo[5,4,0]undec-7-ene (DBU), etc.

The preparation process (a) can be conducted in a substantially wide range of temperature. It is preferable, however, to conduct it at the temperatures in the range of generally about −100 to about 60° C., particularly about −80 to about 40° C. Although said reaction is conducted desirably under normal pressure, it can be operated optionally under elevated pressure or under reduced pressure.

In conducting the preparation process (a), the aimed compound can be obtained, for example, by reacting 1 to 5 moles of difluoromethanesulfonyl chloride to 1 mole of the compound of the formula (II) in a diluent, for example, dichloromethane, in the presence of 1 to 5 moles of pyridine.

The reaction of the above-mentioned preparation process (b) can be conducted in an appropriate diluent. As examples of the diluent used in that case there can be mentioned water; aliphatic, alicyclic and aromatic hydrocarbons (may be optionally chlorinated), for example, hexane, cyclohexane, ligroine, toluene, xylene, dichloromethane, chloroform, carbon tetrachloride, 1,2-dichloroethane, chlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; ketones, for example, acetone, methyl ethyl ketone (MEK), methyl isopropyl ketone, methyl isobutyl ketone (MIBK), etc.; nitriles, for example, acetonitrile, propionitrile, acrylonitrile, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.; sulfones and sulfoxides, for example, dimethyl sulfoxide (DMSO), sulfolane, etc.; bases, for example, pyridine etc.; acids, for example, acetic acid etc.

The preparation process (b) can be conducted in the presence of an acid catalyst and as examples of said acid catalyst there can be mentioned mineral acids, for example, hydrochloric acid, sulfuric acid, nitric acid, hydrobromic acid, sodium hydrogen sulfite, etc.; organic acids, for example, formic acid, acetic acid, trifluoroacetic acid, propionic acid, methanesulfonic acid, benzenesulfonic acid, p-toluenesulfonic acid, etc.

The preparation process (b) can be conducted in a substantially wide range of temperature. It is preferable, however, to conduct it at the temperatures in the range of generally about −100 to about 150° C., particularly about 20 to about 120° C. Although said reaction is conducted desirably under normal pressure, it can be operated optionally under elevated pressure or under reduced pressure.

In conducting the preparation process (b), the aimed compound can be obtained, for example, by reacting 1 to 10 moles of chromium (VI) oxide to 1 mole of the compound of the formula (Ib) in a diluent, for example, acetic acid.

The reaction of the above-mentioned preparation process (c) can be conducted in an appropriate diluent. As examples of the diluent used in that case there can be mentioned water; aliphatic, alicyclic and aromatic hydrocarbons (may be optionally chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene, etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM), etc.; nitriles, for example, acetonitrile, propionitrile, etc.; alcohols, for example, methanol, ethanol, isopropanol, butanol, ethylene glycol, etc.; esters, for example, ethyl acetate, amyl acetate, etc.; acid amides, for example, dimethylformamide (DMF), dimethylacetamide (DMA), N-methylpyrrolidone, 1,3-dimethyl-2-imidazolidinone, hexamethyl phosphoric triamide (HMPA), etc.; sulfones and sulfoxides, for example, dimethyl sulfoxide (DMSO), sulfolane, etc.; bases, for example, pyridine etc.

The preparation process (c) can be conducted in a substantially wide range of temperature. It is preferable, however, to conduct it at the temperatures in the range of generally about −100 to about 60° C., particularly about −80 to about 40° C. Although said reaction is conducted desirably under normal pressure, it can be operated optionally under elevated pressure or under reduced pressure.

In conducting the preparation process (c), the aimed compound can be obtained, for example, by reacting 0.25 to 2 moles of sodium borohydride to 1 mole of the compound of the formula (III) in a diluent, for example, methanol.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds of the aforementioned formula (I), according to the present invention, can be used particularly against paddy field weeds. As examples of the paddy field weeds that can be controlled by using the active compounds, according to the present invention, there can be mentioned the following:

Dicotyledonous plants of the following genera: *Polygonum, Rorippa, Rotala, Lindernia, Bidens, Dopatrium, Eclipta, Elatine, Gratiola, Lindernia, Ludwigia, Oenanthe, Ranunculus, Deinostema*, etc.

Monocotyledonous plants of the following genera: *Echinochloa, Panicum, Poa, Cyperus, Monochoria, Fimbristylis, Sagittaria, Eleocharis, Scirpus, Alisma, Aneilema, Blyxa, Eriocaulon, Potamogeton*, etc.

The active compounds of the aforementioned formula (I), according to the present invention, can be used specifically relating to, for example, the following representative paddy field weeds:

Plant Name in Latin
Dicotyledonous Plants:
*Rotala indica* Koehne
*Lindernia procumbens* Philcox
*Lindernia dubia* L. Penn.
*Lindernia angustifolia*
*Ludwigia prostrata* Roxburgh
*Potamogeton distinctus* A. Benn
*Elatine triandra* Schk
*Oenanthe javanica*
Monocotyledonous Plants:
*Echinochloa oryzicola* Vasing
*Eleocharis acicularis* L.
*Eleocharis kuroguwai* Ohwi
*Cyperus difformis* L.
*Cyperus serotinus* Rottboel
*Scirpus juncoides* Roxburgh
*Monochoria vaginalis* Presi
*Sagittaria pygmaea* Miq
*Alisma canaliculatum* A. Br Et Bouche
*Sagittaria trifolia*
*Monochoria korsakowii*

Moreover, the active compounds of the aforementioned formula (I), according to the present invention, can be effectively used also against, for example, the aforementioned weeds that show resistance against sulfonylurea type herbicides.

The use of the active compounds of the aforementioned formula (I), according to the present invention, however, is not restricted to the use against these kinds of weeds but can be applied against other kinds of paddy field weeds and other weeds than the sulfonylurea type herbicide resistant weeds in a similar manner.

The active compounds, according to the present invention, can be formulated into customary formulation forms on actual application. As such formulation forms there can be mentioned, for example, solutions, wettable powders, emulsions, suspensions, powders, water dispersible granules, tablets, granules, suspo-emulsion concentrates, microcapsules in polymer substance, jumbo formulations, etc.

These formulations can be prepared by per se known methods, for example, by mixing the active compounds with extenders, namely liquid or solid diluents or carriers, and optionally with surface-active agents, namely emulsifiers and/or dispersants and/or foam-forming agents.

As liquid diluents or carriers there can be mentioned, for example, aromatic hydrocarbons (for example, xylene, toluene, alkylnaphthalene, etc.), chlorinated aromatic or chlorinated aliphatic hydrocarbons (for example, chlorobenzenes, ethylene chlorides, methylene chloride, etc.), aliphatic hydrocarbons [for example, cyclohexane etc. or paraffins (for example, mineral oil fractions etc.)], alcohols (for example, butanol, glycols, etc.) and their ethers, esters, etc., ketones (for example, acetone, methyl ethyl ketone, methyl isobutyl ketone, cyclohexanone, etc.), strongly polar solvents (for example, dimethylformamide, dimethyl sulfoxide, etc.), water, etc. In case that water is used as extender, for example, organic solvents can be used as auxiliary solvents.

As solid diluents or carriers there can be mentioned, for example, ground natural minerals (for example, kaolin, clay, talc, chalk, quartz, attapulgite, montmorillonite, diatomaceous earth, etc.), ground synthetic minerals (for example, highly dispersed silicic acid, alumina, silicates, etc.), etc. As solid carriers for granules there can be mentioned crushed and fractionated rocks (for example, calcite, marble, pumice, sepiolite, dolomite, etc.) synthetic granules of inorganic and organic meals, particles of organic materials (for example, saw dust, coconut shells, maize cobs, tobacco stalks, etc.), etc.

As emulsifiers and/or foam-forming agents there can be mentioned, for example, nonionic and anionic emulsifiers [for example, polyoxyethylene fatty acid esters, polyoxyethylene fatty acid alcohol ethers (for example, alkylaryl polyglycol ethers, alkylsulfonates, alkylsulfates, arylsulfonates, etc.)], albumin hydrolysis products, etc.

Dispersants include, for example, lignin sulfite waste liquor, methyl cellulose, etc.

Tackifiers can also be used in formulations (powders, granules, emulsifiable concentrates). As said tackifiers there can be mentioned, for example, carboxymethyl cellulose, natural and synthetic polymers (for example, gum Arabic, polyvinyl alcohol, polyvinyl acetate, etc.).

Colorants can also be used. As said colorants there can be mentioned inorganic pigments (for example, iron oxide, titanium oxide, Prussian Blue, etc,), organic dyestuffs such as alizarin dyestuffs, azo dyestuffs or metal phthalocyanine dyestuffs, and further traces nutrients such as salts of metals such as iron, manganese, boron, copper, cobalt, molybdenum, zinc, etc.

Said formulations can contain the active compounds of the formula (I) in the range of generally 0.01 to 95% by weight, preferably 0.1 to 90% by weight.

The active compounds of the formula (I), according to the present invention, can be used for weed control as themselves or in their formulation forms. And the active compounds of the formula (I) can be used also in combination with known herbicides. Mixed herbicidal compositions with known herbicides can be previously prepared in the final formulation forms or can be prepared by tank mixing when they are used. As the herbicides that can be used as mixed herbicidal compositions in combination with the compounds of the formula (I) there can be mentioned, for example, the following herbicides represented by generic names as typical examples:

acetamide type herbicides: for example, pretilachlor, butachlor, thenylchlor, alachlor, etc.;

amide type herbicides: for example, clomeprop, etobenzanid, etc.;

benzofuran type herbicides: for example, benfuresate etc.;

indandione type herbicides: for example, indanofan etc.;

pyrazole type herbicides: for example, pyrazolate, benzofenap, pyrazoxifen, etc.;

oxazinone type herbicides: for example, oxaziclomefone etc.;

sulfonylurea type herbicides: for example, bensulfuron-methyl, azimsulfuron, imazosulfuron, pyrazosulfuron-ethyl, cyclosulfamuron, ethoxysulfuron, halosulfuron-methyl, etc.;

thiocarbamate type herbicides: for example, thiobencarb, molinate, pyributycarb, etc.;

triazine type herbicides: for example, dimethametryn, simetryn, etc.;

triazole type herbicides: for example, cafenstrole etc.;

quinoline type herbicides: for example, quinclorac etc.;

isoxazole type herbicides: for example, isoxaflutole etc.;

dithiophosphate type herbicides: for example, anilofos etc.;

oxyacetamide type herbicides: for example, mefenacet, flufenacet, etc.;

tetrazolinone type herbicides: for example, fentrazamide etc.;

dicarboxylmide type herbicides: for example, pentoxazone etc.;

oxadiazolon type herbicides: for example, oxadialgyl, oxadiazon, etc.

trione type herbicides: for example, sulcotrione, benzobicyclon, etc.;

phenoxypropionate type herbicides: for example, cyhalofop-butyl etc.;

benzoic acid type herbicides: for example, pyriminobac-methyl, bispyribac-sodium etc.;

diphenyl ether type herbicides: for example, chlomethoxynil, oxyfluorfen, etc.;

pyridine dicarbothioate type herbicides: for example, dithiopyr etc.;

phenoxy type herbicides: for example, MCPA, MCPB, etc.;

urea type herbicides: for example, dymron, cumyluron, etc.;

naphthalenedione type herbicides: for example, quinoclamine etc.;

isoxazolidinone type herbicides: for example, clomazone etc.

The above-mentioned active compounds are known herbicides described in "Pesticide Manual" published in 2000 by British Crop Protect Council.

Further, when the active compounds of the formula (I), according to the present invention, are mixed with safeners, phytotoxicity is reduced by the mixing and a broader weed controlling spectrum is provided and the application as a selective herbicide can be broadened.

As said safeners there can be mentioned, for example, the following compounds represented by generic names or development codes:

AD-67, BAS-145138, benoxacor, cloquintocet-mexyl, cyometrinil, 2,4-D, DKA-24, dichlormid, dymron, fenclorim, fenchlorazole-ethyl, flurazole, fluxofenim, flurazole, isoxadifen-ethyl, mefenpyr-diethyl, MG-191, naphthalic anhydride, oxavetrinil, PPG-1292, R-29148, etc.

The above-mentioned safeners are also described in "Pesticide Manual" published in 2000 by British Crop Protect Council.

Moreover, it is possible to further mix the above-mentioned safeners to a mixed herbicide composition consisting of the compounds of the formula (I), according to the present, invention and an above-mentioned herbicide. By the mixing phytotoxicity is reduced and a broader weed controlling spectrum is provided and the application as a selective herbicide can be broadened.

Surprisingly, some of the mixed herbicide compositions consisting of a compound of the present invention and a known herbicide and/or safener can show synergistic effects.

In case of using the active compounds of the formula (I) they can be directly used as such or used in formulation forms such as ready-to-use solutions, emulsifiable concentrates, tablets, suspensions, powders, pastes or granules, or used in use forms prepared by further dilution. The active compounds of the present invention can be applied by means of, for example, watering, spraying, atomizing, granule application, etc.

The active compounds of the formula (I) can be used at any stages before and after germination of plants. They can be also mixed into the soil before sowing.

The application amount of the active compounds of the formula (I) can be varied in a substantial range. It is fundamentally different depending upon the properties of effects to be desired. In case of using as herbicide, there can be mentioned application amounts in the range of, for example, about 0.0001 to about 4 kg, preferably about 0.01 to about 3 kg as active compound per hectare.

As already mentioned above, it is possible to treat all plants and their parts according to the invention. In a preferred embodiment, wild plant species and cultivars, or those obtained by conventional biological breeding, such as crossing or protoplast fusion, and parts thereof, are treated. In a further preferred embodiment, transgenic plants and cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the cultivars which are in each case commercially available or in use are treated according to the invention. Cultivars are to be understood as meaning plants having certain properties ("traits") and which have been obtained by conventional breeding, by mutagenesis or by recombinant DNA techniques. They can be varieties, bio- or genotypes.

Depending on the plant species or cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention also in combination with other agrochemically active compounds, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeafe (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to cultivars having these genetic traits or genetic traits still to be developed, which plants will be developed and/or marketed in the future.

The plants listed can be treated according to the invention in a particularly advantageous manner with the compounds of the formula (I) or the active compound mixtures according to the invention where in addition to the effective control of the weeds, the above-mentioned synergistic effects with the transgenic plants or plant cultivators occur. The preferred ranges stated above for the active compounds or mixtures also apply to the treatment of these plants. Particular emphasis is given to the treatment of plants with the compounds or mixtures specifically mentioned in the present text.

Then further specific examples of the preparation and application of the compounds of the formula (I) according to present invention, will be shown by the following examples. The present invention, however, should not be restricted only to them in any way.

SYNTHESIS EXAMPLE 1

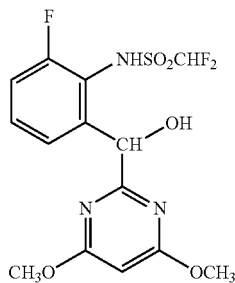

2-Fluoro-6-[(4,6-dimethoxypyrimidin-2-yl)hydroxymethyl]aniline 1.6 g (5.28 mmol) was dissolved in dichloromethane (13 ml) and pyridine 0.91 g (11.46 mmol) was added thereto. The solution was cooled to −5° C. and a solution of difluoromethanesulfonyl chloride 1.73 g (11.46 mmol) in dichloromethane (2 ml) was added thereto. The reaction solution was stirred at room temperature for 4 days and after addition of water it was extracted three times with dichloromethane. The organic layer was washed with 1N hydrochloric acid and water. After drying, dichloromethane was distilled off under reduced pressure and the obtained oily substance was purified by column chromatography using 1:3 mixed solvent of ethyl acetate and hexane as eluent to obtain the objective 2-fluoro-6-[(4,6-dimethoxypyrimidin-2-yl)hydroxymethyl]-N-difluoromethanesulfonanilide 0.94 g (yield 42%) as pale yellow crystals.

$^1$H-NMR(300 MHz,CDCl$_3$)δ3.99 (6H,s),4.97 (1H,d), 5.99 (1H,s), 6.13 (1H,d),6.61 (1H,t),7.07-7.13 (1H,m),7.23-7.29 (1H,m),7.51-7.53 (1H,m), 10.57(1H,br).

SYNTHESIS EXAMPLE 2

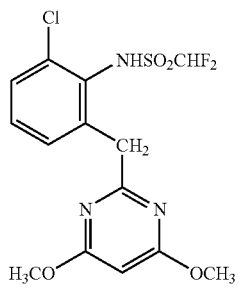

2-Chloro-6-[(4,6-dimethoxypyrimidin-2-yl)methyl] aniline 1.54 g (5.51 mmol) was dissolved in dichloromethane (12 ml) and pyridine 0.87 g (11.01 mmol) was added thereto. The solution was cooled to −5° C. and a solution of difluoromethanesulfonyl chloride 1.66 g (11.01 mmol) in dichloromethane (2 ml) was added thereto. The reaction solution was stirred at room temperature for 4 days and after addition of water it was extracted three times with dichloromethane. After the organic layer had been washed with water and dried, dichloromethane was distilled off under reduced pressure and the objective 2-chloro-6-[(4,6-dimethoxypyrimidin-2-yl)methyl]-N-difluoromethanesulfonanilide 1.2 g (yield 55%) was obtained as white crystals from the obtained oily substance by column chromatography using 1:6 mixed solvent of ethyl acetate and hexane as eluent.

$^1$HNMR(300 MHz,CDCl$_3$)δ3.94 (6H,s),4.30(2H,s),5.92 (1H,s),6.74(1H,t), 7.18-7.21(1H,m),7.33-7.38(2H,m),11.09 (1H,br).

The following compound was obtained by the same process as the above-mentioned Synthesis Example 2:

2-Fluoro-6-[(4,6-dimethoxytriazin-2-yl)methyl]-N-difluoromethanesulfonanilide.

$^1$H-NMR(300MHz,CDCl$_3$)δ4.05(6H,s),4.22(2H,s),6.56 (1H,t), 7.07-7.28(3H,m),10.16(1H,s).

SYNTHESIS EXAMPLE 3

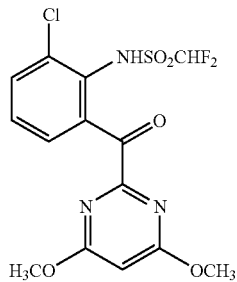

2-Chloro-6-[(4,6-dimethoxypyrimidin-2-yl)methyl]-N-difluoromethanesulfonanilide 0.4 g (1.02 mmol) was dissolved in acetic acid (6 ml) and chromium (VI) oxide 0.31 g (3.05 mmol) was added thereto. The solution was heated to 30° C. and stirred for 6 hours. After stirring further 12 hours at room temperature, the reaction solution was diluted with water and extracted three times with diethyl ether. The organic layer was washed with water. After drying, diethyl ether was distilled off under reduced pressure and the objective 2-chloro-6-[(4,6-dimethoxypyrimidin-2-yl)carbonyl]-N-difluoromethanesulfonanilide 0.28 g (yield 67%) was obtained as white crystals from the obtained oily substance by column chromatography using 1:3 mixed solvent of ethyl acetate and hexane as eluent.

$^1$H-NMR(300 MHz,CDCl$_3$)δ3.93(6H,s),6.19(1H,s),6.34 (1H,t), 7.37-7.43(1H,m),7.63-7.69 (2H,m).

The following compound was obtained by the same process as the above-mentioned Synthesis Example 3:

2-Fluoro-6-[(4,6-dimethoxytriazin-2-yl)carbonyl]-N-difluoromethanesulfonanilide.

$^1$H-NMR(300 MHz,CDCl$_3$)δ4.10(6H,s),6.48(1H,t),7.36 (1H,m), 7.45(1H,t),7.55(1H,d),9.08(1H,s).

SYNTHESIS EXAMPLE 4

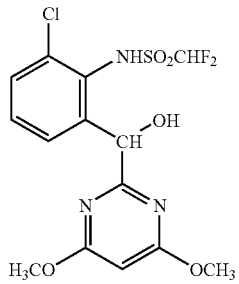

2-Chloro-6-[(4,6-dimethoxypyrimidin-2-yl)carbonyl]-N-difluoromethanesulfonanilide 0.83 g (2.04 mmol) was dissolved in methanol 30 ml and, after cooling it to 5° C., sodium borohydride 0.15 g (4.07 mmol) was added thereto while stirring. Then the solution was stirred at room temperature for 2 hours. The reaction solution was distilled off under reduced pressure and the obtained crystals were dissolved in water and dichloromethane and neutralized with citric acid. The organic layer was separated and the water layer was further extracted three times with dichloromethane. After the organic layer had been washed with water and dried, dichloromethane was distilled off under reduced pressure to obtain the objective 2-chloro-6-[(4,6-dimethoxypyrimidin-2-yl)hydroxymethyl]-N-difluoromethanesulfonanilide 0.79 g (yield 95%) as white crystals.

$^1$H-NMR(300MHz,CDCl$_3$)δ3.99(6H,s),4.99(1H,br),5.99(1H,s), 6.24(1H,s),6.76(1H,t),7.27-7.30(1H,m),7.39-7.42(1H,m), 7.64-7.67(1H,m),10.62(1H,br).

The compounds obtained in the same manner as the above-mentioned Synthesis Examples 1-4, are shown, together with the compounds synthesized in Synthesis Examples 1-4, in the following Table 1 and their physical and chemical properties are shown in Table 2.

TABLE 1

| compound. No. | X | Y | R$^1$ | R$^2$ |
|---|---|---|---|---|
| 1 | F | CH | H | OH |
| 2 | F | N | H | OH |
| 3 | Cl | CH | H | OH |
| 4 | Cl | N | H | OH |
| 5 | Br | CH | H | OH |
| 6 | Br | N | H | OH |
| 7 | I | CH | H | OH |
| 8 | I | N | H | OH |
| 9 | F | CH | H | H |
| 10 | F | N | H | H |
| 11 | Cl | CH | H | H |
| 12 | Cl | N | H | H |
| 13 | Br | CH | H | H |
| 14 | Br | N | H | H |
| 15 | I | CH | H | H |
| 16 | I | N | H | H |
| 17 | F | CH | C=O | |
| 18 | F | N | C=O | |
| 19 | Cl | CH | C=O | |
| 20 | Br | CH | C=O | |
| 21 | Br | N | C=O | |
| 22 | I | CH | C=O | |
| 23 | I | N | C=O | |

TABLE 2

| Compound No. | Physical & Chemical Properties ($^1$H-NMR (300 MHz, CDC$_3$)δ) |
|---|---|
| 1 | 3.99 (6H, s), 4.97 (1H, d), 5.99 (1H, s), 6.13 (1H, d), 6.61 (1H, t), 7.07-7.13 (1H, m), 7.23-7.29 (1H, m), 7.51-7.53 (1H, m), 10.57 (1H, br). |
| 2 | 4.08 (6H, s), 6.10 (1H, s), 6.58 (1H, t), 7.13 (1H, t), 7.26-7.33 (1H, m), 7.47 (1H, d), 9.60 (1H, s). |
| 3 | 3.99 (6H, s), 4.99 (1H, br), 5.99 (1H, s), 6.24 (1H, s), 6.76 (1H, t), 7.27-7.30 (1H, m), 7.39-7.42 (1H, m), 7.64-7.67 (1H, m), 10.62 (1H, br). |
| 9 | 3.97 (6H, s), 4.26 (2H, s), 5.94 (1H, s), 6.59 (1H, t), 7.05-7.13 (1H, m), 7.16-7.23 (2H, m), 11.14 (1H, br). |
| 10 | 4.05 (6H, s), 4.22 (2H, s), 6.56 (1H, t), 7.07-7.28 (3H, m), 10.16 (1H, s). |
| 11 | 3.94 (6H, s), 4.30 (2H, s), 5.92 (1H, s), 6.74 (1H, t), 7.18-7.21 (1H, m), 7.33-7.38 (2H, m), 11.09 (1H, br). |
| 12 | 4.02 (6H.s) 4.34 (2H, s) 6.68 (1H, t) 7.22 (1H) 7.32 (1H) 7.41 (1H) 9.98 (1H, br). |
| 17 | 3.97 (6H, s), 6.20 (1H, s), 6.51 (1H, t), 7.29-7.34 (1H, m), 7.39-7.46 (1H, m), 7.55-7.58 (1H, m), 11.14 (1H, br). |
| 18 | 4.10 (6H, s), 6.48 (1H, t), 7.36 (1H, m), 7.45 (1H, t), 7.55 (1H, d), 9.08 (1H, s), |
| 19 | 3.93 (6H, s), 6.19 (1H, s), 6.34 (1H, t), 7.37-7.43 (1H, m), 7.63-7.69 (2H, m). |

REFERENCE EXAMPLE 1

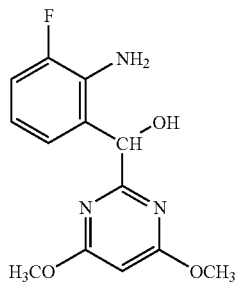

2-Fluoro-6-[(4,6-dimethoxxypyrimidin-2-yl)carbonyl] aniline 2.68 g (9.67 mmol) was dissolved in methanol 80 ml and, after cooling it to 5° C., sodium borohydride 0.73 g (19.33 mmol) was added thereto while stirring. Then the solution was stirred at room temperature for 2 hours. The reaction solution was distilled off under reduced pressure and the obtained crystals were dissolved in water and dichloromethane. The organic layer was separated and the water layer was further extracted three times with dichloromethane. After the organic layer had been washed with water and dried, dichloromethane was distilled off under reduced pressure to obtain the objective 2-fluoro-6-[(4,6-dimethoxypyrimidin-2-yl)hydroxymethyl]aniline 2.66 g (yield 98%) as white crystals.

$^1$H-NMR(300MHz, CDCl$_3$)δ3.94(6H,s),4.74(3H,m),5.84 (1H,d), 5.94(1H,s),6.66-6.73(1H,m),6.88-6.95(1H,m),7.13-7.15(1H,m).

REFERENCE EXAMPLE 2

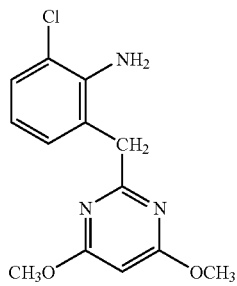

To 10 ml of a methanol solution of 2-chloro-6-[1-(4,6-dimethoxxypyrimidin-2-yl)-1-methylthiomethyl]aniline 0.6 g (1.84 mmol) and 0.88 g (3.68 mmol) of nickel (II) chloride hexahydrate, 0.28 g (7.37 mmol) of sodium borohydride was added at 0-10° C. and the reaction solution was stirred at room temperature for 2 hours. After the reaction solution was distilled off under reduced pressure, aqueous ammonia and dichloromethane were added and the insoluble matter was filtered off. The organic layer was separated and the water layer was further extracted three times with dichloromethane. After the organic layer had been washed with water and dried, dichloromethane was distilled off under reduced pressure and the obtained crystals were washed with n-hexane to obtain the objective 2-chloro-6-[(4,6-dimethoxypyrimidin-2-yl)methyl]aniline 0.48 g (yield 93%) as white crystals.

$^1$H-NMR(300MHz,CDCl$_3$)δ3.91(6H,s),4.01(2H,s),5.18 (2H,s), 5.81(1H,s),6.62-6.67(1H,m),7.14-7.17(2H,m).

REFERENCE EXAMPLE 3

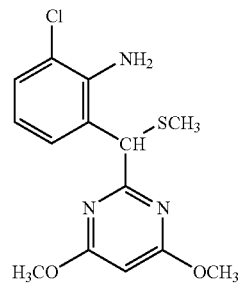

2-Chloroaniline 5.2 g (26.0 mmol) was dissolved in dichloromethane (200 ml) and the solution was cooled to −70° C. To the cooled solution a dichloromethane (10 ml) solution of tert-butyl hypochlorite 2.82 g (26.0 mmol) was added dropwise and the solution was stirred at −70° C. for 10 minutes. To the obtained reaction solution a dichloromethane (20 ml) solution of 2-methylthiomethyl-4,6-dimethoxypyrimidine 3.38 g (26.0 mmol) was added dropwise and the solution was stirred at −70° C. for 40 minutes. To the obtained reaction solution 28% sodium methoxide methanol solution (9 ml) was added and the solution was stirred until it came to room temperature. Water was added to the reaction solution and the organic layer was separated. The water layer was further extracted twice with dichloromethane. After the organic layer had been washed with water and dried, dichloromethane was distilled off under reduced pressure and the objective 2-chloro-6-[1-(4,6-dimethoxypyrimidin-2-yl)-1-methylthiomethyl]aniline 7.00 g (yield 83%) was obtained as oily substance from the obtained oily substance by column chromatography using 1:8 mixed solvent of ethyl acetate and hexane as eluent.

$^1$H-NMR(300MHz,CDCl$_3$)δ2.04(3H,s),3.93(6H,s),5.07 (1H,br), 5.14(1H,s),5.90(1H,s),6.67(1H,t),7.19(1H,dd),7.42 (1H,dd).

Comparative compound

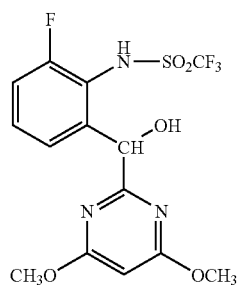

C-1

(C-1 is a similar compound disclosed in WO 96/41799)

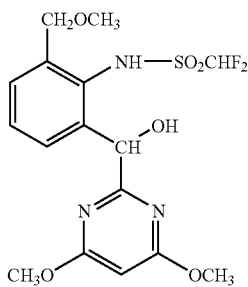

C-2

(C-2 is a similar compound disclosed in Japanese Laid-open Patent Publication No. 44546/2000)

TEST EXAMPLE 1

Test for Herbicidal Effect Against Paddy Field Weeds

Preparation of Formulation of the Active Compound

Carrier: DMF 5 Parts by Weight

Emulsifier: Benzyloxy Polyglycol Ether 1 Part by Weight

A formulation of an active compound is obtained as an emulsifiable concentrate by mixing 1 part by weight of the active compound with the above-mentioned amount of the carrier and emulsifier. A prescribed amount of the formulation is diluted with water.

In a green house seeds or tubers of *Scirpus juncoides* Roxburgh, *Monochoria vaginalis* Presl, annual broad-leaved weeds (*Lindemia procumbens* Philcox, *Rotala indica* Koehne, *Elatine triandra* Schk, *Ammannia multiflora* Roxb., etc.), *Cyperus serotinus* Rottboel were inoculated in a 500 cm² pot filled with paddy field soil. Then water was poured to a depth of about 2-3 cm. Five days and 13 days after inoculation, a prescribed, diluted solution of the formulation of each active compound, prepared according to the aforementioned preparation method, was applied to the surface of water. After the treatment the water depth of 3 cm was maintained and the herbicidal effect was examined after 3 weeks from the treatment.

The herbicidal effect was rated 100% in the case of complete death and as 0% in the case of no herbicidal effect. In case of showing higher than 80% herbicidal effect, it is evaluated as practical as herbicide.

The study results with the compounds No. 1, 3, 11 and 17 and the comparative compound No. C-1 as specific examples are shown in the following Table 3 and Table 4.

TABLE 3

| | Application 5 days after inoculation | | | | |
|---|---|---|---|---|---|
| | | herbicidal effect | | | |
| compound. No. | amount (g ai/ha) | *Scirpus juncoides* | *Monochoria vaginalis* | broad-leaved weeds | *Cyperus serotinus* |
| 1 | 30 | 100 | 100 | 100 | 100 |
| | 15 | 100 | 100 | 100 | 100 |
| 3 | 30 | 100 | 100 | 100 | 100 |
| 11 | 60 | 100 | 100 | 100 | 100 |
| 17 | 30 | 100 | 100 | 100 | 100 |
| comparative C-1 | 30 | 80 | 80 | 80 | 80 |
| | 15 | 70 | 60 | 50 | 70 |

TABLE 4

| | Application 13 days after inoculation | | | | |
|---|---|---|---|---|---|
| | | herbicidal effect | | | |
| compound. No. | amount (g ai/ha) | *Scirpus juncoides* | *Monochoria vaginalis* | broad-leaved weeds | *Cyperus serotinus* |
| 1 | 30 | 100 | 100 | 100 | 100 |
| | 15 | 100 | 100 | 95 | 95 |
| 3 | 30 | 100 | 100 | 100 | 100 |
| 11 | 60 | 100 | 100 | 100 | 95 |
| 17 | 30 | 100 | 100 | 100 | 100 |
| comparative C-1 | 30 | 70 | 60 | 60 | 60 |
| | 15 | 60 | 50 | 40 | 60 |

TEST EXAMPLE 2

Test for Residual Effectiveness Against Paddy Field Weeds

In a green house a 1000 cm² pot was filled with paddy field soil and water was poured to a depth of about 2 to 3 cm. A prescribed, diluted solution of the above-mentioned Test Example 1, was applied to the surface of water. After the prescribed time after the treatment (just after treatment, 1 week, 2 weeks, 3 weeks, 4 weeks, 5 weeks, 6 weeks and 7 weeks after treatment), seeds or tubers of the weeds to be tested *Scirpus juncoides* Roxburgh, *Monochoria vaginalis* Presl, annual broad-leaved weeds (*Lindernia procumbens* Philcox, *Rotala indica* Koehne, *Elatine triandra* Schk, *Ammannia multiflora* Roxb., etc.), *Cyperus serotinus* Rottboel and *Sagittaria pygmaea* Miq. were inoculated. Three weeks after the inoculation each herbicidal effect was examined.

The evaluation of the residual effectiveness was shown as the period (number of weeks) of maintaining herbicidal effect of higher than 80%, after the evaluation of herbicidal effect had been conducted in the similar manner as the above-mentioned Test Example 1.

The study results with the compounds No. 1 and No. 11, and the comparative compounds No. C-1 and No. C-2 as specific examples are shown in the following Table 5.

TABLE 5

| compound. No. | amount (g ai/ha) | period showing sufficient residual herbicidal effectiveness (week) | | | | |
|---|---|---|---|---|---|---|
| | | Scirpus juncoides | Monochoria vaginalis | broad-leaved weeds | Cyperus serotinus | Sagittaria pygmaea |
| 1 | 60 | 6 | 4 | 3 | 3 | 3 |
| 11 | 60 | 4 | 3 | 4 | — | 4 |
| comparative C-1 | 60 | 2 | <1 | <1 | 1 | 1 |
| comparative C-2 | 60 | 2 | 2 | 2 | — | 3 |

TEST EXAMPLE 3

Test for Herbicidal Effect Against Sulfonylurea Resistant Weeds

In a green house seeds of *Scirpus juncoides* Roxburgh (collected in Iwamizawa area, Hokkaido), *Lindernia procumbens* Philcox (collected in Kazo area, Saitama Pref.), *Lindernia procumbens* Philcox (collected in Higashi-Hiroshima area, Hiroshima Pref.), *Elatine triandra* Schk (collected in Kazo area, Saitama Pref.), all of which were confirmed as sulfonylurea resistant, were inoculated in a 20 cm² cup filled with paddy field soil. Then water was poured to a depth of about 2 to 3 cm. At the beginning of emergence of each weed, a prescribed, diluted solution of the formulation of each active compound prepared in the same manner as the above-mentioned Test Example 1 was applied to the surface of water. After the treatment the water depth of 3 cm was maintained and the herbicidal effect was examined after 3 weeks from the treatment. The evaluation of the herbicidal effect was conducted in the same manner as the above-mentioned Test Example 1. In case of showing higher than 80% herbicidal effect, it is evaluated as practical as herbicide. In consideration of the possibility that the biological properties including herbicide resistance of the plants grown in different areas might be different, sulfonylurea resistant *Lindernia procumbens* Philcox collected in two different areas were used in the present tests. The study results with the compounds No. 1, 3, 11 and 17 and the comparative compound No. C-1 as specific examples are shown in the following Table 6.

TABLE 6

| | | herbicidal effect against sulfonylurea resistant weeds | | | |
|---|---|---|---|---|---|
| compound. No. | amount (g ai/ha) | Scirpus juncoides (collected in Iwamizawa area, Hokkaido) | Lindernia procumbens (collected in Kazo area, Saitama Pref.) | Lindernia procumbens (collected in Higashi-Hiroshima area, Hiroshima Pref.) | Elatine triandra (collected in Kazo area, Saitama Pref.) |
| 1 | 60 | 100 | 100 | 100 | 100 |
| | 30 | 100 | 95 | 100 | 100 |
| 3 | 60 | 100 | 100 | — | — |
| | 30 | 100 | 100 | — | — |
| 11 | 60 | 100 | 100 | — | — |
| | 30 | 100 | 100 | — | — |
| 17 | 60 | 100 | 100 | — | — |
| | 30 | 100 | 95 | — | — |
| comparative C-1 | 60 | 70 | 60 | 80 | 70 |
| | 30 | 60 | 40 | 50 | 60 |

TEST EXAMPLE 4

Test for Phytotoxicity to Transplanted Rice

The phytotoxicity to transplanted rice was evaluated under the conditions with more shallow planting depths than usual depth of 2 cm, simulating the severe condition for herbicides to cause rice injury in the paddy. In a greenhouse 2 to 2.5 leaf-stage of rice (var. Nipponbare) was transplanted at three different depths, in a 1000 cm² pot filled with paddy field soil. Then water was poured to a depth of about 2 to about 3 cm. Five days after transplanting, a prescribed, diluted solution of the formulation of each active compound, prepared in the same manner as the above-mentioned Test Example 1, was applied to the surface of water. After the treatment the water depth of 3 cm was maintained and the rice injury was examined after 2 weeks from the treatment. The rice injury was rated 100% in the case of complete death and as 0% in the case of no injury. In case of showing less than 20% injury, it is evaluated as practical as rice herbicide.

The study results with the compound No. 11, and the comparative compounds No. C-1 and C-2 a specific examples are shown in the following Table 7.

TABLE 7

| Application 5 days after transplanting | | | | |
|---|---|---|---|---|
| | amount | phytotoxicity to transplanted rice | | |
| compound No. | (g ai/ha) | depth 2 cm | depth 0.5 cm | depth 0 cm |
| 11 | 60 | 10 | 15 | 15 |
| comparative C-1 | 60 | 20 | 35 | — |
| comparative C-2 | 60 | 30 | 30 | 40 |

TEST EXAMPLE 5

Test for Phytotoxicity to Direct-seedling Rice and Herbicidal Effect Against Paddy Field Weeds In a greenhouse seeds of *Scirpus juncoides* Roxburgh, *Monochoria vaginalis* Presl, *Cyperus difformis* L., annual broad-leaved weeds (*Lindernia procumbens* Philcox, *Rotala indica* Koehne, *Elatine triandra* Schk, *Ammannia multiflora* Roxb.) and rice (var.: Nipponbare and RD-23) were inoculated in a 500 cm² pot filled with paddy field soil. Then water was poured to a depth of about 0 to about 0.5 cm, to be a wet condition. At two leaf-stage of rice, a prescribed, diluted solution of the formulation of each active compound, prepared in the same manner as the above-mentioned Test Example 1, was sprayed over the pots with plants. At 2 days after the treatment, the water depth of 3 cm was maintained and the herbicidal effect and rice injury was evaluated at 3 weeks and 2 weeks after the treatment, respectively.

The herbicidal effect and rice injury were rated 100% in the case of complete death and as 0% in the case of no effect or injury. In case of showing higher than 80% herbicidal effect and less than 20% injury, it is evaluated as practical as rice herbicide.

The study results with the compound No.3 and No. 11 and the comparative compound No. C-2 as specific examples are shown in the following Table 8.

TABLE 8

| | Application at two leaf-stage of rice (spray) | | | | | | |
|---|---|---|---|---|---|---|---|
| | | herbicidal effect | | | | Phytotoxicity to direct-seedling rice | |
| compound No. | amount (g ai/ha) | Cyperus difformis L. | Scirpus juncoides | Monochoria vaginalis | broad-leaved weeds | Nippon- bare | RD-23 |
| 3 | 50 | 100 | 100 | 100 | 100 | 20 | 10 |
| 11 | 50 | 100 | 90 | 100 | 100 | 10 | 10 |
| comparative C-2 | 50 | 100 | 90 | 100 | 100 | 50 | 30 |

FORMULATION EXAMPLE 1

Granule

To a mixture of the compound of the present invention No. 1 (0.4 parts), bentonite (montmorillonite) (39.6 parts), talc (58 parts) and ligninsulfonate salt (2 parts), water (25 parts) were added, well kneaded, made into granules of 10 to 40 mesh by an extrusion granulator and dried at 40 to 50° C. to obtain granules.

FORMULATION EXAMPLE 2

Granules

Clay mineral particles (99.8 parts) having particle diameter distribution in the range of 0.2 to 2 mm are put in a rotary mixer. While rotating it, the compound of the present invention No. 1 (0.2 parts) are sprayed together with a liquid diluent, wetted uniformly and dried at 40 to 50° C. to obtain granules.

FORMULATION EXAMPLE 3

Emulsifiable Concentrate

The compound of the present invention No. 1 (30 parts), xylene (55 parts), polyoxyethylene alkyl phenyl ether (8 parts) and calcium alkylbenzenesulfonate (7 parts) are mixed and stirred to obtain an emulsifiable concentrate.

FORMULATION EXAMPLE 4

Wettable Powder

The compound of the present invention No. 1 (15 Parts), a mixture of white carbon (hydrous amorphous silicon oxide fine powders) and powder clay (1:5) (80 parts), sodium alkylbenzenesulfonate (2 parts) and sodium alkylnaphthalenesulfonate-formalin-condensate (3 parts) are mixed in powder to obtain a wettable powder.

FORMULATION EXAMPLE 5

Water Dispersible Granule

The compound of the present invention No. 1 (20 Parts), sodium ligninsulfonate (30 parts), bentonite (15 parts) and calcined diatomaceous earth powder (35 parts) are well mixed, added with water, extruded with 0.3 mm screen and dried to obtain water dispersible granules.

The invention claimed is:

1. A compound of the formula (I)

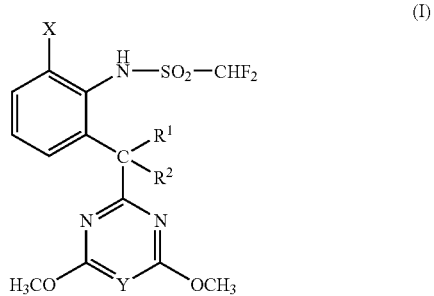

wherein
X represents halogen,
Y represents N,
$R^1$ represents hydrogen, and
$R^2$ represents hydrogen or hydroxy, or
$R^1$ and $R^2$ together with the carbon atom to which they are attached form C=O.

2. A compound according to claim 1, wherein
X represents fluorine or chlorine,
Y represents N,
$R^1$ represents hydrogen, and
$R^2$ represents hydrogen or hydroxy, or
$R^1$ and $R^2$ together with the carbon atom to which they are attached form C=O.

3. A process for preparing a compound of the formula (I) according to claim 1,

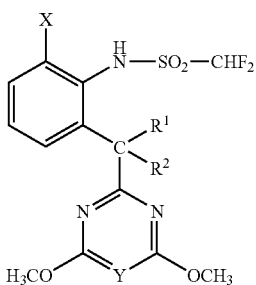

(I)

wherein
X, Y, R¹ and R² are defined as in claim 1, comprising,
a) reacting a compound of the formula (II)

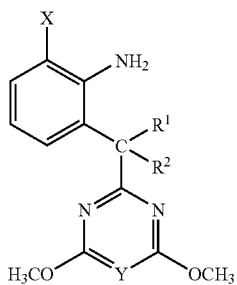

(II)

wherein
X, Y, R¹ and R² have the same definition as aforementioned,
with difluoromethanesulfonyl chloride in the presence of an inert solvent, and optionally, in the presence of an acid binding agent, or b) when R¹ and R² together form C=O with the carbon atom to which they are attached:
reacting a compound of the formula (Ib)

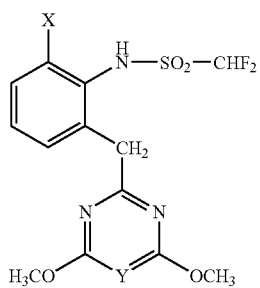

(Ib)

wherein
X and Y have the same definition as aforementioned,
with an oxidizing agent in the presence of an inert solvent, and optionally, in the presence of an acid catalyst, or c) when R¹ represents hydrogen, and R² represents hydroxy:
reacting a compound of the formula (Ic)

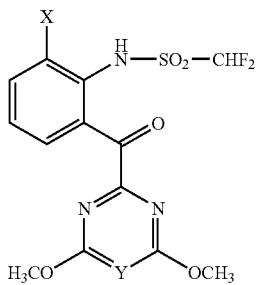

(Ic)

wherein
X and Y have the same definition as aforementioned,
with an alkali metal hydride complex compound or a borane complex in the presence of an inert solvent.

4. A herbicidal composition comprising at least one compound of the formula (I) according to claim 1.

5. A process for combating paddy field weeds, comprising, contacting a paddy field weed or its habitat with at least one compound of the formula (I) according to claim 1.

6. A process for the preparation of a herbicidal composition, comprising, mixing a compound of the formula (I) according to claim 1 with one or more extenders, one or more surface active agents, or a combination thereof.

7. A compound according to claim 1, wherein
X represents fluorine,
Y represents N,
R¹ represents hydrogen, and
R² represents hydroxy.

* * * * *